US00PP10784P

United States Patent [19]

Collicutt et al.

[11] Patent Number: Plant 10,784

[45] Date of Patent: Feb. 9, 1999

[54] MONARDA PLANT NAMED 'PETITE DELIGHT'

[75] Inventors: Lynn M. Collicutt, Lowe Farm; Campbell G. Davidson, Morden, both of Canada

[73] Assignee: Her Majesty the Queen in Right of Canada as represented by the Minister of Agriculture, Ottawa, Canada

[21] Appl. No.: 864,347

[22] Filed: May 28, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

A new and distinct variety of perennial Monarda or Bee-Balm plant is provided that exhibits a unique dwarf stature and good winter hardiness. The blossoms exhibits an attractive light pink-purple to light purple coloration (as illustrated). Dense dark green and glossy foliage is formed that contrasts well with the blossom coloration. The low-growing growth habit of the new variety can readily be distinguished from that of the 'Marshalls Delight' variety (non-patented in the United States).

2 Drawing Sheets

SUMMARY OF THE INVENTION

The new and distinctive perennial Monarda (Bee Balm) variety of the present invention was the result of a breeding program involving open pollinated and controlled crosses that was carried out at Morden, Manitoba, Canada. The initial female parent (i.e., the seed parent) was *Monarda didyma* 'Cambridge Scarlet' (non-patented in the United States) and the initial male parent (i.e., the pollen parent) was *Monarda fistulosa menthaefolia* (non-patented in the United States). The initial cross created the 'Souris' variety (non-patented in the United States). Plants designated '60-1', '62-0', '64-8', '66-1', '76-1' and '75-1' were created in subsequent generations through the open pollination of the 'Souris' variety and offspring that were derived from the 'Souris' variety. Plants '76-1' and '75-1' next were crossed to create a plant designated '78-1'. The open polination of plant '78-1' resulted in the creation of the 'Marshall's Delight' variety (non-patented in the United States). See, *HortScience,* 24(3):525 (1989) where the 'Marshalls Delight' variety is discussed. Next, the 'Marshall's Delight' variety was open pollinated to form a plant designated '86-2'. Plant '86-2' subsequently was open pollinated to form offspring from which the new variety of the present invention was selected during 1988. The single plant of the new variety found among the offspring initially was designated '88-12'.

It was found that the new Monarda variety of the present invention:

(a) forms attractive light pink-purple to light purple blossoms,
(b) exhibits attractive dense dark green and glossy foliage,
(c) exhibits a dwarf growth habit that can be readily distinguished from that of the 'Marshall's Delight' variety, and
(d) exhibits good winter hardiness.

The low-growing dwarf growth habit of the new variety of perennial Monarda plant of the present invention is particularly noteworthy, and can be used to quickly differentiate the new variety from previously known varieties, such as the 'Marshall's Delight' variety. The flowers, stems, and foliage of the new variety are aromatic and typical in this regard to that of other *Monarda didyma* and *Monarda fistulosa* plants. The shiny dark green foliage of the new variety contrasts well with the light purple blossoms.

The new variety well meets the needs of the horticultural industry and can be grown as attractive ornamentation in parks, gardens, public areas, and residential landscapes. Large mass plantings are particularly attractive. Floral designs can be sculpted using the new variety in combination with other low-growing herbaceous plants. The new variety can be included in traditional formal beds where it provides an attractive mid- to late-season bloom. The plants of the new variety also can be used as specimen plants or as borders dividing sections of floral beds or to define a boundary in a planting area.

The characteristics of the new variety have been found to be homogeneous and stable and have been shown to be transmissble by asexual reproduction using rhizome and softwood stem cuttings, division, and tissue culture. It is been found that propagation by the use of rhizome cuttings is very successful when applied to the new variety and can be as a means to rapidly multiply the new variety. Approximately 30 rhizome cuttings can be obtained from two or three year-old plants. Rhizome segments having a length of approximately 2.5 to 5 cm. can be harvested in early spring or fall possessing approximately 0.5 to 1 cm. of terminal growth, inserted into a potting media, and grown in a greenhouse or outdoors while protected. For best results rhizome cuttings should be selected that have minimal vegetative leaf growth. Softwood stem cuttings can be taken early in the growing season and rooted under intermittent mist. It has been found that rooting success drops dramatically when propagation using stem cuttings is attempted during mid-summer. It is not essential to utilize a hormone during rooting; however, such hormone usage has been found to accelerate the rooting speed. A two-year old plant commonly will yield approximately six divisions.

The new variety has been named 'Petite Delight'.

BRIEF DESCRIPTION OF THE PHOTOGRAPHS

The accompanying photographs show, as nearly true as it is reasonably possible to make the same in color illustrations of this character, typical specimens of the plant parts of the new variety. The Monarda plants described herein were approximately two years of age and were photographed while growing outdoors during mid-summer 1995 at Morden, Manitoba, Canada.

DETAILED DESCRIPTION

Figure 1:
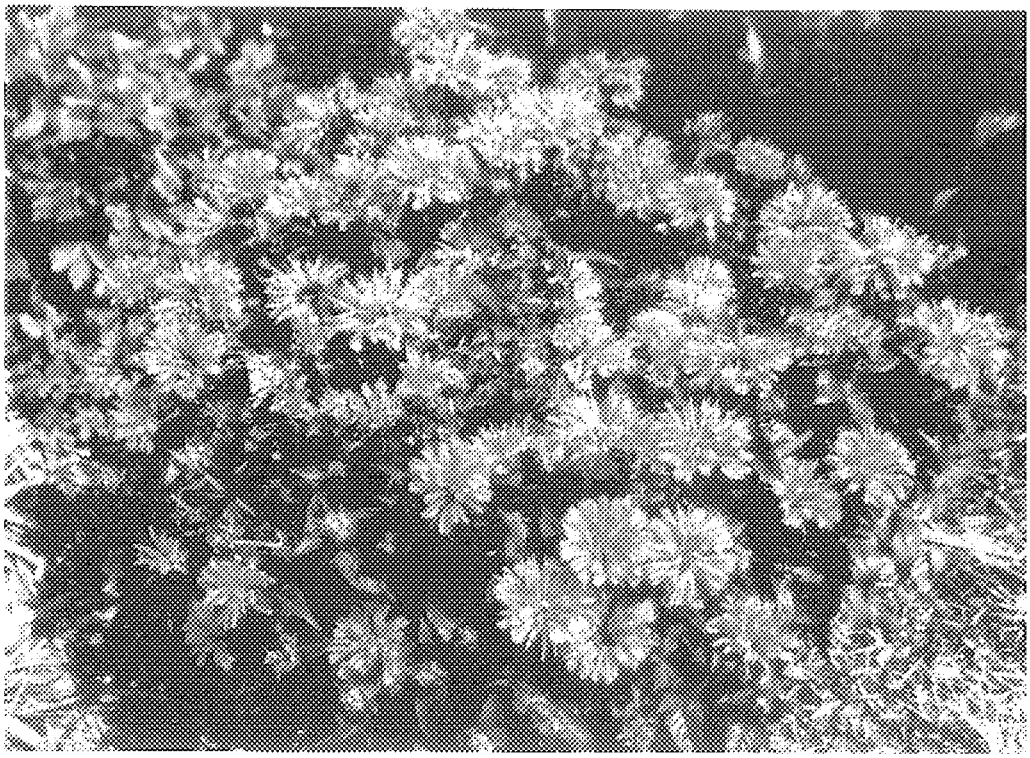
FIG. 1 illustrates a flowering plant of the new variety while growing in the landscape. The compact dwarf stature, dense dark green glossy foliage, and light pink-purple to light purple blossoms are apparent.
Figure 2:
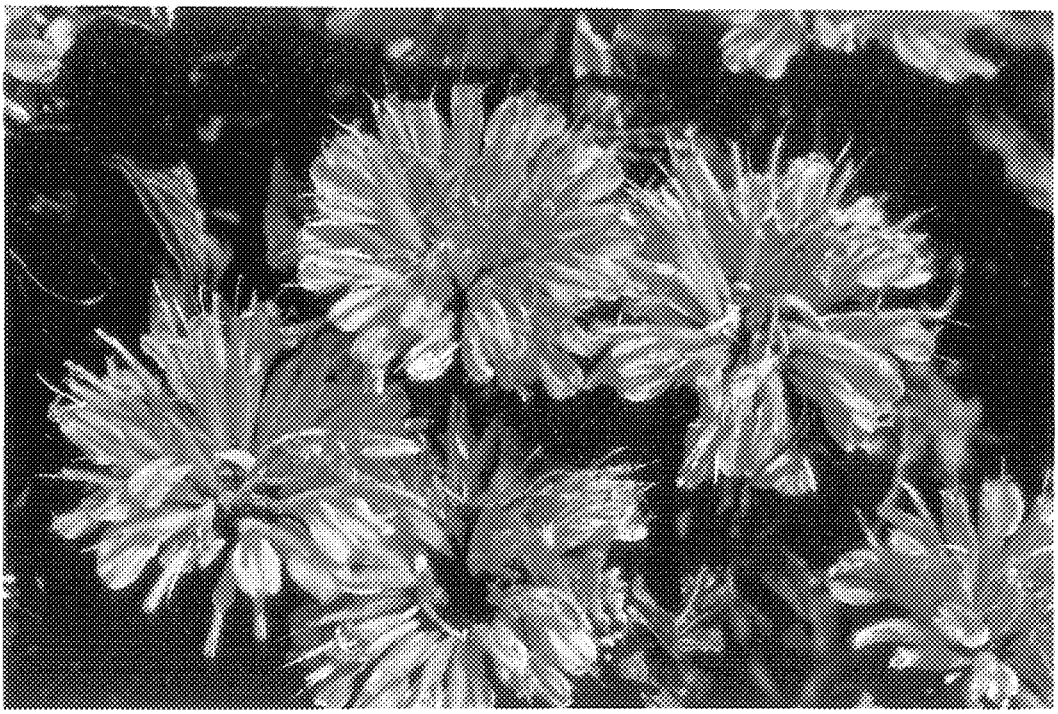
FIG. 2 illustrates an enlarged view of typical specimens of the blossoms and foliage of the new variety.

The chart used in the identification of the colors is that of The Royal Horticultural Society (R.H.S. Colour Chart). Common color terms are to be accorded their ordinary dictionary significance. The description is based on the observation of two year-old plants of the new variety while being grown outdoors in the landscape during the summer at Morden, Manitoba, Canada.

Botanical classification: *Monarda didyma*×*Monarda fistulosa menthaefolia*, cv. 'Petite Delight'.

Plant:

*Growth habit.*—Dwarf, compact, and round to oval in configuration.

*Size.*—Commonly approximately 25 to 30 cm. in height and width. This can be compared to a height and width of approximately 50 to 60 cm. for the 'Marshall's Delight' variety.

Foliage:

*Size.*—Leaves commonly measure approximately 6 cm. in length and approximately 3.5 cm. in width. The leaf size commonly is variable depending upon the location along the stem. The leaf shape varies from ovate-lanceolate to chordate with the more chordate leaves being present towards the tip of the stem. The leaflets tend to be truncate at the base with an attenuate tip. The leaflet texture is moderately coarse due to the presence of pubescence. The leaflet aspect commonly changes from substantially horizontal at the base to more ascending at the tip. The leaves commonly tend to be somewhat smaller with shorter internode lengths than those of the 'Marshalls Delight' variety. More specifically, the internode distance is approximately 20 mm. shorter than that of the 'Marshall's Delight' variety. For instance, when measured at the lower portion of a main stem, the internode distance averaged 29.92 mm. vs. 49.0 mm. for the 'Marshall's Delight' variety.

*Margins.*—Serrate.

*General appearance.*—Dense, dark green and glossy. The foliage typically is more glossy than that of the 'Marshall's Delight' variety. When viewed from a distance the appearance is similar to that of a bedding Chrysanthemum plant. More specifically, from a distance the new variety is mounding with terminal influorescence, multipe main stems and exhibits a dense appearance.

*Color.*—Dark green, Yellow-Green Group 147A on the upper surface and Green Group 137 A on the under surface.

*Venation.*—Is typical for the genus with a central midrib and commonly 10 to 12 veins in a predominantly opposite arrangement. The veins appear to be slightly sunken on the upper surface and slightly protruding on the under surface. However, such difference is slight. Very small veins commonly are visible which connect the main veins of the leaf. Pubescence tends to be slightly longer on the veins and on the midrib than on the remaining leaf tissue. Tiny hairs also commonly are visible along the left margins.

*Stems.*—Four-sided, pubescent, and near Yellow-Green Group 144A in coloration. Stem lengths vary with growing conditions and the stems commonly are approximately 25 to 30 cm. in length.

Inflorescence:

*Buds.*—The coloration changes as the buds develop. Initially the buds are green and of substantially the same coloration as the stems. They next gradually lighten in coloration to a light yellow-green coloration prior to full maturation.

*Flowers.*—Typical of the species with respect to size and configuration.

*Borne.*—Terminally, and dense compound (verticillaster).

*Size.*—Approximately 6 to 6.5 cm. in diameter.

*Color.*—Light pink-purple to light purple with shades of Red-Purple Group 64A, Red-Purple Group 72B, and Red-Violet Group 80A. The coloration varies somewhat depending upon the age of the blossoms and the season of the year. For instance, the intensity of the coloration tends to diminish and to become lighter with blossom age. This can be compared to a typical blossom coloration of Red-Purple Group 63B for the 'Marshall's Delight' variety.

*Flower duration.*—Approximatley 6 to 8 weeks beginning during mid-August at Morden, Manitoba, Canada.

*Reproductive organs.*—Typical of the species. Viable pollen is formed and the flowers are fertile.

*Fragrance.*—The aroma is typical of the species. The leaves and stems also are fragrant.

Development:

*Vegetation.*—Good vigor. The growth rate is generally equivalent to that of the species. Even though the plant is a genetic dwarf, it is not slow growing. The early spring growth commonly reaches full size in approximately six weeks.

*Culture.*—Plants should be cut back in the spring to remove older foliage and to promote new growth. Care should always be exercised so as not to damage the crown of the plant. The plants preferably are dead-headed after flowering to improve visual appearance. The regrowth of the foliage after flowering is good thereby serving to maintain a fresh green appearance late in the growing season and throughout the fall.

*Disease resistance.*—During the course of observations to date powdery mildew has not posed a major problem. Some rust (*Puccinia menthol Pers.*) has been observed, but such rust involvement generally has taken place late in the season and was not severe. In comparative trials the new variety was rated very good for disease resistance when compared to other commonly-grown Monarda varieties.

*Hardiness.*—Plants are hardy to at least Agriculture Canada Zone 3 with no winter protection other than naturally occuring snowfall. See Ouellette and Sherk, Woody Ornamental Plant Zonation III, Suitability Map for Probable Winter Survival of Ornamental Trees and Shrubs, *Can. J. Plant Sci.,* 47:3513–3518(1967). Due to low-growing habit of the new variety, natural snow cover is believed likely to be capable of extending the growing range to even colder regins.

We claim:

1. A new distinct variety of Monarda plant having the following combination of characteristics:

(a) forms attractive light pink-purple to light purple blossoms, (b) exhibits attractive dense dark green and glossy foliage, (c) exhibits a dwarf growth habit that can be readily distinguished from that of the 'Marshall's Delight' variety, and (d) exhibits good winter hardiness;

substantially as herein shown and described.

* * * * *